US006990426B2

(12) United States Patent
Yoon et al.

(10) Patent No.: US 6,990,426 B2
(45) Date of Patent: Jan. 24, 2006

(54) DIAGNOSTIC METHOD AND APPARATUS USING LIGHT

(75) Inventors: Gil-won Yoon, Seoul (KR); Hong-sig Kim, Seongnam (KR); Kye-jin Jeon, Suwon (KR); Jong-youn Lee, Yongin (KR); Kun-kook Park, Yongin (KR); Su-jin Kim, Daejeon (KR); Hoon-jong Jwa, Seoul (KR)

(73) Assignee: Samsung Electronics Co., Ltd., Suwon (KR)

( * ) Notice: Subject to any disclaimer, the term of this patent is extended or adjusted under 35 U.S.C. 154(b) by 38 days.

(21) Appl. No.: 10/387,552

(22) Filed: Mar. 14, 2003

(65) Prior Publication Data

US 2003/0236647 A1    Dec. 25, 2003

(30) Foreign Application Priority Data

Mar. 16, 2002    (KR) ...................... 10-2002-0014277

(51) Int. Cl.
    *A61B 5/02*    (2006.01)
(52) U.S. Cl. ...................................... 702/139; 702/191
(58) Field of Classification Search .................. 702/21, 702/26, 139, 189–195; 600/476–484, 500–508
    See application file for complete search history.

(56) References Cited

U.S. PATENT DOCUMENTS

| 3,593,704 | A | * | 7/1971 | Schwab ........................ 600/500 |
| 4,869,253 | A | * | 9/1989 | Craig et al. .................. 600/323 |
| 5,137,023 | A | * | 8/1992 | Mendelson et al. ......... 128/633 |
| 5,206,807 | A | | 4/1993 | Hatke et al. |
| 5,273,036 | A | * | 12/1993 | Kronberg et al. ........... 600/310 |
| 5,482,036 | A | | 1/1996 | Diab et al. |
| 5,499,627 | A | | 3/1996 | Steuer et al. |
| 5,800,348 | A | | 9/1998 | Kaestle |
| 5,830,137 | A | * | 11/1998 | Scharf ......................... 600/323 |
| 5,833,602 | A | * | 11/1998 | Osemwota ................... 600/310 |
| 5,862,805 | A | * | 1/1999 | Nitzan ......................... 128/898 |

(Continued)

FOREIGN PATENT DOCUMENTS

CN    1 120 427    4/1996

(Continued)

OTHER PUBLICATIONS

Cui et al., In Vivo Reflectance of Blood and Tissue as a Function of Light Wavelength, Jun. 1990, IEEE Transactions on Biomedical Engineering, vol. 37, No. 6, pp. 632 and 634.*

(Continued)

*Primary Examiner*—Marc S. Hoff
*Assistant Examiner*—Craig Steven Miller
(74) *Attorney, Agent, or Firm*—Lee & Morse, P.C.

(57) ABSTRACT

A diagnosis method and apparatus for measuring blood hemoglobin concentration, oxygen saturation, pulse rate, respiration rate, or degree of aging of blood vessels using light includes an input/output unit for receiving a command for measurement from a user and for providing information on the result of a measurement to the user; a control unit for receiving the command for measurement from the input/output unit and for generating a control signal; a light generating unit for generating at least two light beams for measurement according to the control signal; a light receiving unit for receiving the light beams transmitted through an object that is subject to measurement and for converting the received light beams into electrical signals; and a data processing unit for processing the electrical signals received from the light receiving unit and for outputting information on the result of a predetermined measurement.

33 Claims, 9 Drawing Sheets

U.S. PATENT DOCUMENTS

| | | | |
|---|---|---|---|
| 5,941,837 A | 8/1999 | Amano et al. | |
| 6,011,985 A * | 1/2000 | Athan et al. | 600/322 |
| 6,067,462 A | 5/2000 | Diab et al. | |
| 6,325,761 B1 * | 12/2001 | Jay | 600/485 |
| 6,398,727 B1 * | 6/2002 | Bui et al. | 600/300 |
| 6,702,752 B2 * | 3/2004 | Dekker | 600/484 |

FOREIGN PATENT DOCUMENTS

| | | |
|---|---|---|
| EP | 0 555 553 A2 | 8/1993 |
| EP | 0 555 553 A3 | 8/1993 |
| JP | 1-232928 | 9/1989 |
| JP | 5-269116 | 10/1993 |
| JP | 6-507485 | 8/1994 |
| JP | 7-213500 | 8/1995 |
| JP | 9-135819 | 5/1997 |
| JP | 10-216114 | 8/1998 |
| JP | 10-216115 | 8/1998 |
| JP | 2000-23928 | 1/2000 |
| JP | 3054437 | 6/2000 |
| JP | 2000-217797 | 8/2000 |
| JP | 2002-65621 | 3/2002 |

OTHER PUBLICATIONS

Sherebrin et al., Frequency Analysis of the Peripheral Pulse Wave Detected in the Fingerwith a Photoplethysmograph, Mar. 1990, IEEE Tranactions on Biomedical Engineering, vol. 37, No. 3, pp. 313. See entire document.*

Jeon, Kye Jin, et al., *, Journal of Biomedical Optics 7(1):45-50 (Jan. 2002).

*Entitled: "Noninvasive total hemoglobin measurement".

* cited by examiner

DIAGNOSTIC METHOD AND APPARATUS USING LIGHT

BACKGROUND OF THE INVENTION

1. Field of the Invention

The present invention relates to a diagnostic method and apparatus using light. More particularly, the present invention relates to a method and apparatus for measuring blood hemoglobin concentration, oxygen saturation, pulse rate, respiration rate, and degree of aging of blood vessels using light.

2. Description of the Related Art

Hemoglobin in red blood cells is responsible for supplying oxygen throughout the human body and is essential for the normal function of every cell in the body. A reduced supply of oxygen to the body restricts the intercellular energy metabolism in tissues, and a lack of oxygen for a prolonged period of time results in death. Hemoglobin content is used as a measure of anemia and is measured to qualify a blood donor and to determine the volume of blood that may safely be taken from a blood donor.

There is a need for real-time monitoring of a patient's condition by measuring hemoglobin concentration, oxygen saturation, pulse rate, respiration rate, and degree of aging of blood vessels, especially in patients that are bleeding as the result of a traffic accident and in patients in need of a surgical operation. In addition, there is a need for introducing a convenient method that enables a health care provider to check frequently biological conditions of children and pregnant females, in particular, by measuring these parameters.

Conventionally, hemoglobin concentration is measured in a medical institute for therapeutic or prophylactic purposes through chemical analysis of blood drawn from the body. The measurements of pulse rate, respiration rate, or degree of aging of blood vessels are typically conducted only by health care providers. Therefore, a convenient method enabling the general public to personally measure each of these parameters at home is required.

SUMMARY OF THE INVENTION

The present invention provides a method and apparatus for measuring blood hemoglobin concentration, oxygen saturation, pulse rate, respiration rate, and degree of aging of blood vessels using light.

According to an aspect of the present invention, there is provided a diagnosis apparatus using light, including an input/output unit for receiving a command for measurement from a user and for providing information on the result of a measurement to the user; a control unit for receiving the command for measurement from the input/output unit and for generating a control signal; a light generating unit for generating at least two light beams, each light beam having an initial intensity, for measurement according to the control signal; a light receiving unit for detecting the intensity of each of the at least two light beams after transmission through an object that is subject to measurement and for converting the received light beams into electrical signals; and a data processing unit for processing the electrical signals received from the light receiving unit and for outputting information on the result of a predetermined measurement to the input/output unit.

Preferably, the light generating unit includes a digital-to-analog converter for receiving the control signal from the control unit and for converting the received control signal into an analog signal; a light emitting diode driver for driving a light emitting diode to generate the at least two light beams according to the analog signal; and a light radiator for radiating the generated light beams onto the object.

Preferably, the light receiving unit includes a photodetector for detecting the intensities of the at least two light beams after transmission through the object and for converting the detected light beam intensities into analog electrical signals; a low-pass filter for filtering out a high frequency component of the analog electrical signals (representing the intensity of the at least two light beams received from the photodetector); and an analog-to-digital converter for converting the analog electrical signals (representing the intensity of the light beams, from which the high-frequency component has been removed) into digital electrical signals.

In one embodiment of the present invention, the data processing unit may include a ratio calculation portion for receiving the electrical signals (representing the intensity of the at least two light beams received by the light receiving unit) from the light receiving unit and for calculating, for each wavelength of the at least two light beams, a ratio of the intensity of the light received by the light receiving unit with respect to the initial intensity of the light radiated from the light generating unit; and a hemoglobin concentration and oxygen saturation calculation portion for calculating a hemoglobin concentration value using the ratio calculated by the ratio calculation portion based on a correlation between light intensity variations and hemoglobin concentrations and for calculating an oxygen saturation value using the calculated hemoglobin concentration value.

In another embodiment of the present invention, the data processing unit may include a pulse rate calculation portion for receiving the electrical signals (representing the intensity of the at least two light beams output from the light receiving unit) from the light receiving unit, for extracting a pulse wave signal having a frequency corresponding to an average pulse rate per minute for humans from the received electrical signals, and for calculating a pulse rate based on an average time interval between peaks detected from the extracted pulse wave signal.

In yet another embodiment of the present invention, the data processing unit may include a respiration rate calculation portion for receiving the electrical signals (representing the intensity of the at least two light beams output from the light receiving unit) from the light receiving unit, for extracting a respiration signal having a frequency corresponding to an average respiration rate per minute for humans from the received electrical signals, and for calculating a respiration rate based on an average time interval between peaks detected from the extracted respiration signal.

In still another embodiment of the present invention, the data processing unit may include a degree of aging of blood vessels calculation portion for receiving the electrical signals (representing the intensity of the at least two light beams output from the light receiving unit) from the light receiving unit, for extracting a first pulse wave signal having a frequency corresponding to an average pulse rate per minute for humans from the received electrical signals, for differentiating the extracted first pulse wave signal into a second pulse wave signal to detect inflection points therein, for calculating a diagnostic index for the degree of aging of blood vessels using the values of the inflection points, and for calculating a degree of aging of blood vessels using the calculated diagnostic index, based on a correlation between the degrees of aging of blood vessels and diagnostic indices therefor.

In addition, the data processing unit may further include a data storage portion for storing measured results and for outputting to the input/output unit a calculated result according to a control signal of the control unit.

According to another aspect of the present invention, there is provided a diagnosis method using light, including (a) receiving a command for measurement from a user; (b) generating a control signal according to the received command for measurement; (c) generating at least two light beams, each light beam having an initial intensity, for measurement according to the control signal; (d) radiating the at least two light beams onto an object that is subject to measurement, detecting the intensities of the at least two light beams after transmission through the object, and converting the detected intensities of the at least two light beams into electrical signals; and (e) processing the electrical signals to obtain information on the result of a predetermined measurement.

Preferably, generating the at least two light beams includes (c1) receiving the control signal and converting the received control signal into an analog signal; (c2) generating the at least two light beams according to the analog signal; and (c3) radiating the generated light beams onto the object.

Preferably, radiating the light beams onto an object includes (d1) detecting the intensities of the at least two light beams after transmission through the object and converting the detected light beam intensities into analog electrical signals; (d2) filtering out a high frequency component of the analog electrical signals (representing the intensity of the transmitted light beams); and (d3) converting the analog electrical signals (representing the intensity of the light beams, from which the high-frequency component has been removed) into digital electrical signals.

In one embodiment of the present invention, processing the electrical signals may include (e1) calculating, for each wavelength of the at least two light beams, a ratio of the intensity of the light beam detected in (d) with respect to the initial intensity of the light generated in (c); (e2) calculating a hemoglobin concentration value using the ratio calculated in (e1) based on a correlation between light intensity variations and hemoglobin concentrations and calculating an oxygen saturation value using the calculated hemoglobin concentration value.

In another embodiment of the present invention, processing the electrical signals may include extracting a pulse wave signal having a frequency corresponding to an average pulse rate per minute for humans from the electrical signals obtained in (d); and calculating a pulse rate based on an average time interval between peaks detected from the extracted pulse wave signal.

In yet another embodiment of the present invention, processing the electrical signals may include extracting a respiration signal having a frequency corresponding to an average respiration rate per minute for humans from the electrical signals obtained in (d); and calculating a respiration rate based on an average time interval between peaks detected from the extracted respiration signal.

In still another embodiment of the present invention, processing the electrical signals may include extracting a first pulse wave signal having a frequency corresponding to an average pulse rate per minute for humans from the electrical signals obtained in (d); differentiating the extracted first pulse wave signal into a second pulse wave signal to detect inflection points therein; calculating a diagnostic index for the degree of aging of blood vessels using the values of the inflection points; and calculating a degree of aging of blood vessels using the calculated diagnostic index, based on a correlation between the degrees of aging of blood vessels and diagnostic indices therefor.

The diagnosis method may further include providing the result of the predetermined measurement to the user, wherein the user may be remotely located from the object subject to measurement. The diagnosis method may also further include storing the information on the result of the predetermined measurement.

In any of the aspects and embodiments of the present invention, preferably, the at least two light beams have different wavelengths. Also preferably, the at least two light beams are selected from a range of wavelengths in which the extinction coefficient for water is smaller than that of hemoglobin and have a wavelength no longer than 1300 nm. Preferably, the at least two light beams are isobestic and each has a wavelength selected from the group consisting of 422 nm, 453 nm, 499 nm, 529 nm, 546 nm, 569 nm, 584 nm, 805 nm, and 1300 nm.

Another feature of an embodiment of the present invention is to provide a computer readable medium having embodied thereon a computer program for any of the above-described diagnosis methods.

BRIEF DESCRIPTION OF THE DRAWINGS

The above features and advantages of the present invention will become more apparent to those of ordinary skill in the art by describing in detail preferred embodiments thereof with reference to the attached drawings in which.

DETAILED DESCRIPTION OF THE INVENTION

Korean Patent Application No. 2002-14277, filed on Mar. 16, 2002, and entitled: "Diagnostic Method and Apparatus Using Light," is incorporated by reference herein in its entirety.

Several embodiments of a diagnosis method and apparatus for measuring blood hemoglobin concentration, oxygen saturation, pulse rate, respiration rate, and degree of aging of blood vessels using light, according to the present invention, will now be described with reference to the appended drawings.

Figure 1:
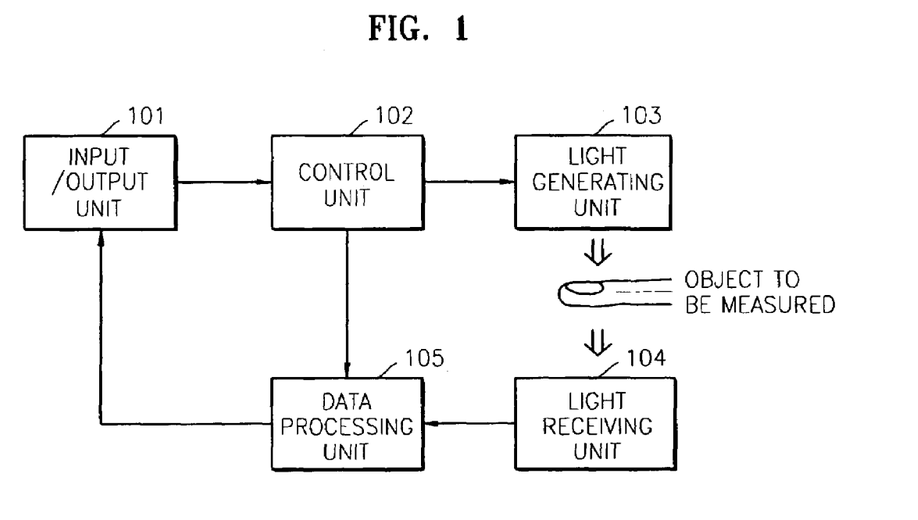
FIG. 1 is a block diagram illustrating the overall configuration of a diagnosis apparatus using light, according to an embodiment of the present invention.

FIG. 1 shows the overall configuration of a diagnosis apparatus using light, according to an embodiment of the present invention. The diagnosis apparatus of FIG. 1 includes an input/output unit 101, a control unit 102, a light generating unit 103, a light receiving unit 104, and a data processing unit 105.

In operation, a user provides the input/output unit 101 a parameter to be measured, such as blood hemoglobin concentration, oxygen saturation, pulse rate, respiration rate, degree of aging of blood vessels (hereinafter "DOA"). The input/output unit 101 informs the user of the result of a measurement of the input parameter. The input/output unit 101 may use a button, a mouse, a keyboard, or the like as an input device and may use a computer monitor, a liquid crystal display (LCD), or other display as an output device for providing the information regarding the result of the measurement to the user. Alternatively, information on the result of a measurement may be transmitted via, for example, an RS232 port to an external personal computer (PC), a personal digital assistant (PDA), or the like. Accordingly, the user may be remotely located from the patient and the object subject to the measurement.

The control unit 102 receives a command to measure a predetermined parameter from the input/output unit 101 and transmits information on the parameter to the light generating unit 103, the light receiving unit 104, and the data processing unit 105. The control unit 102 also verifies the operation of each unit of the diagnosis apparatus.

Figure 2:
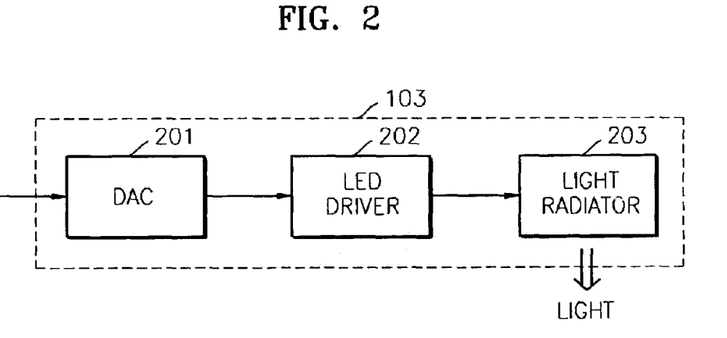
FIG. 2 is a detailed block diagram of the light generating unit of FIG. 1.

The light generating unit 103 generates at least two light beams having predetermined wavelengths for measurement according to the information on the parameter received from the control unit 102. A detailed configuration of the light generating unit 103 is shown in FIG. 2. Referring now to FIG. 2, the light generating unit 103 may include a digital-to-analog converter (DAC) 201 for converting a digital control signal received from the control unit 102 into an analog signal, a light emitting diode (LED) driver 202 for receiving the analog control signal and for driving an LED that generates the at least two light beams having predetermined wavelengths, and a light radiator 203 for externally radiating the at least two light beams onto an object to be measured.

Figure 3:
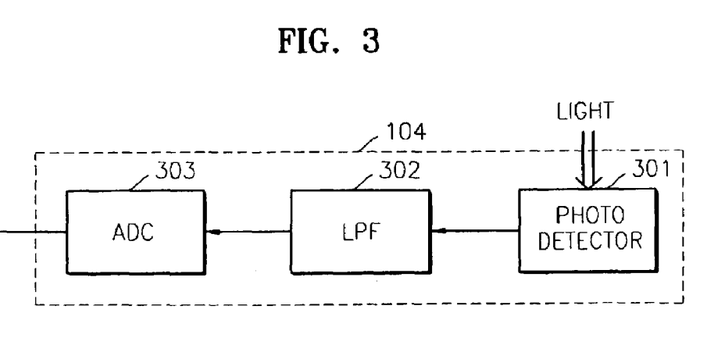
FIG. 3 is a detailed block diagram of the light receiving unit of FIG. 1.

Referring back to FIG. 1, the light receiving unit 104 measures the intensities of the light beams transmitted through the object, among the light beams emitted from the light generating unit 103, and converts the light beams to electrical signals. The configuration of the light receiving unit 104 is shown in detail in FIG. 3. Referring now to FIG. 3, the light receiving unit 104 may include a photodetector 301 for detecting the intensities of the light beams transmitted through the object and for converting the light beams to electrical signals, a low-pass filter (LPF) 302 for filtering out a high frequency component of the electrical signals representing the intensity of the light beams received from the photodetector 301, and an analog-to-digital converter (ADC) 303 for converting the analog electrical signals, from which the high-frequency component has been removed by the LPF 302, into digital electrical signals.

Referring back to FIG. 1, the data processing unit 105 receives the electrical signals representing the intensity of the received light beams from the light receiving unit 104 and processes the received electrical signals to provide information on the result of a measurement of the input parameter, such as blood hemoglobin concentration, oxygen saturation, pulse rate, respiration rate, and DOA of blood vessels. The configuration of the data processing unit 105 is shown in detail in FIG. 4.

Figure 4:
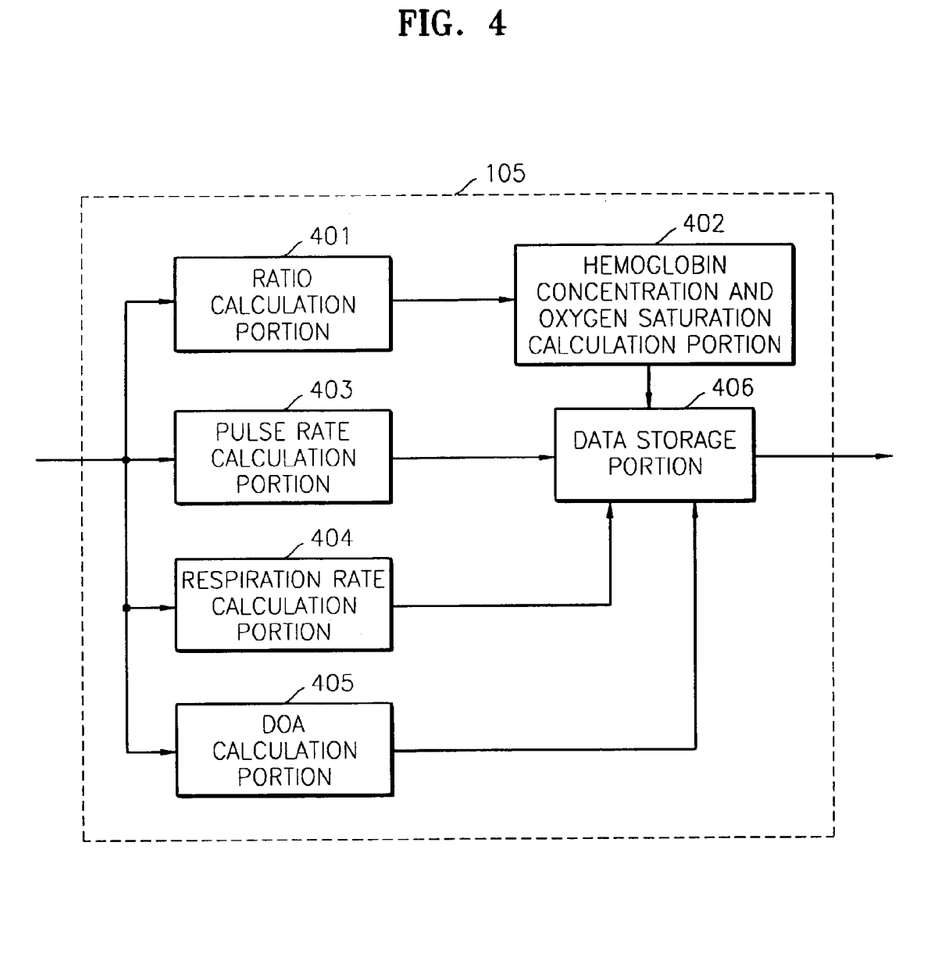
FIG. 4 is a detailed block diagram of the data processing unit of FIG. 1.

Referring to FIG. 4, the data processing unit 105 may include a data storage portion 406, a ratio calculation portion 401, a hemoglobin concentration and oxygen saturation calculation portion 402, a pulse rate calculation portion 403, a respiration rate calculation portion 404, and a DOA calculation portion 405. The function of each of these elements will now be explained.

The ratio calculation portion 401 receives the digital intensity signals for the received light beams output from the light receiving unit 104 and, for each of the light beams, calculates a ratio of the intensity of the light received by the light receiving unit 104 with respect to the initial intensity of the light radiated from the light generating unit 103 onto the object that was subjected to the measurement.

The hemoglobin concentration and oxygen saturation calculation portion 402 calculates a hemoglobin concentration value using the ratio calculated by the ratio calculation portion 401 based on a correlation between light intensity variations and hemoglobin concentrations, and calculates an oxygen saturation value using the calculated hemoglobin concentration value. A method for calculating oxygen saturation following the calculation of hemoglobin concentration is briefly described below. Oxygen saturation, which is expressed as a percentage of the concentration of oxyhemoglobin bound to oxygen with respect to total hemoglobin concentration, is measured to quantify the amount of oxygen saturated in blood for the normal function of body cells. To measure oxygen saturation, red light and infrared light are transmitted through biological tissues, the absorbance for each wavelength of the radiated lights is measured using pulses of arterial blood, and a ratio of the measured absorbances is calculated as the oxygen saturation. Most of the light radiated on the human body is absorbed by bones, tissues, etc., which are not involved in pulsing, via predetermined travelling paths, and only 1–2% of the light radiated is absorbed by arterial blood, which induces pulses. By measuring the intensity of the light transmitted through the body, the light absorbencies of the pulsing components and the non-pulsing components for each wavelength of the radiated light beams can be calculated, which will give the light absorbance of hemoglobin present in the arterial blood. As a result, the oxygen saturation of hemoglobin can be determined from the absorbance ratio between the two wavelengths of light.

The pulse rate calculation portion 403 receives the digital signals corresponding to the intensities of the received light beams from the light receiving unit 104, extracts a pulse wave signal having a frequency corresponding to an average pulse rate per minute for humans from the received digital signal, and calculates a pulse rate per minute based on an average time interval between peaks detected from the extracted pulse wave signal.

More specifically, the pulse rate calculation portion 403 receives the digital signals corresponding to the intensities of the light beams sequentially transmitted through a predetermined body site to be measured, e.g., a finger, and extracts only a pulse wave signal having a frequency in accordance with an average pulse rate for humans from the received signals using, for example, software such as a filtering program. Differentiation is performed on the pulse wave signal passed through a filter, and inflection points, at which the slope changes from positive to negative, are detected from the differentiated pulse wave signal. When an inflection point has a value greater than a predetermined threshold value, the inflection point is stored as a peak. An average time interval between detected peaks is calculated, and the number of peaks in a 60 second interval is calculated based on the average time interval as a pulse rate.

A received signal, as described above, may be classified into pulse waves, velocity pulse waves, or acceleration pulse waves according to the signal processing technique applied to the received signal. In general, pulse waves refer to the original waveform of body pulses and are used to characterize the original body pulses. However, the original body pulses have too smooth a waveform for variations to be detected. To compensate for this smoothness, the original body waves are differentiated for clinical applications. These differential body waves are called "velocity pulse waves." Velocity pulse waves are used to analyze variations in the waveform of the original body waves. Velocity pulse waves, i.e., differential pulse waves, are used in currently available pulse wave detectors. However, variations in the original body waves cannot be fully analyzed with velocity pulse waves. For this reason, velocity pulse waves are further differentiated into "acceleration pulse waves" for clinical uses. Recent advances in the medical engineering field, especially in the diagnosis of circulatory system disorders, have put greater importance on the use of electrocardiograms, photocardiograms, cardiac catheterizations, and the like. Although various experiments have been conducted on pulse waves, the consequence of pulse waves as a diagnostic index tends to be underestimated due to the simple pulse waveform and its nature of being susceptible to a number of factors. Pulse waves are considered to be significant only to some extent in a limited number of peripheral vascular diseases. However, based on the possibility of measuring cardiac failure by the palpation of the radial artery, research on pulse waves as a measure of cardiac reserve or cardiac insufficiency has been conducted. Measuring cardiac failure by the palpation of the radial artery is based on the fact that certain types of cardiac disorders lead to a typical alternation in the pulse waveform resulting from abnormal hemokinetic behaviors. In addition, pulse waves can be used as a diagnostic index for vascular diseases, such as arterial occlusive disorders, alterations in vascular elasticity, etc.

Figure 5:
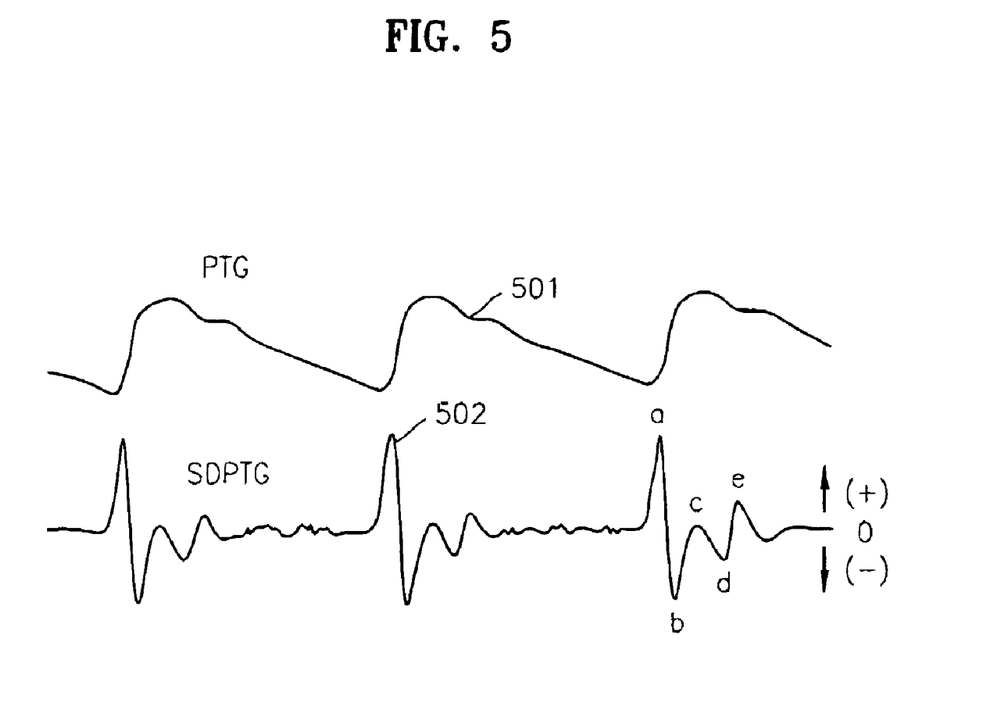
FIG. 5 is an exemplary pulse wave measured in accordance with an embodiment of the present invention.

An example of a pulse wave is illustrated in FIG. 5. Referring now to FIG. 5, a waveform indicated by reference numeral 501 and "PTG" corresponds to an original body pulse wave, and a waveform indicated by reference numeral 502 and "SDPTG" corresponds to an acceleration pulse wave generated by differentiating the waveform 501 twice.

Referring back to FIG. 4, the respiration rate calculation portion 404 receives the digital signals corresponding to the intensities of the received light beams from the light receiving unit 104, extracts a respiration signal having a frequency in accordance with the average respiration rate per minute for humans, and calculates a respiration rate based on an average time interval between peaks detected from the extracted respiration signal.

The method for calculating the respiration rate per minute will be described in detail. A respiration signal having a frequency in accordance with the average respiration rate for humans is extracted from a pulse wave signal using a bandpass filter. This bandpass filter used may be implemented using software.

Normal adults breathe 10–20 times a minute in a stable state and up to about 45 times a minute when exercising. Therefore, the respiration signal has a relatively low frequency of about 0.1–0.5 Hz with respect to the pulse wave signal and can be separated from the pulse wave signal using an appropriate bandpass filter. Inflection points, at which the slope changes from positive to negative, are detected from the separated respiration signal that has passed a digital filter. Since one inflection point corresponds to one breath, the respiration rate per minute can be calculated by counting the number of inflection points in a 60 second interval.

The DOA calculation portion 405 receives the digital signals corresponding to the intensities of the received light beams, extracts a first pulse wave signal having a frequency in accordance with the average pulse rate for humans, differentiates the extracted first pulse wave signal into a second pulse wave signal to detect inflection points therein, calculates a diagnostic index for the degree of aging of blood vessels using the values of the inflection points, and calculates a degree of aging of blood vessels for a subject using the calculated diagnostic index, based on a correlation between the degrees of aging of blood vessels and diagnostic indices therefor.

Figure 6:
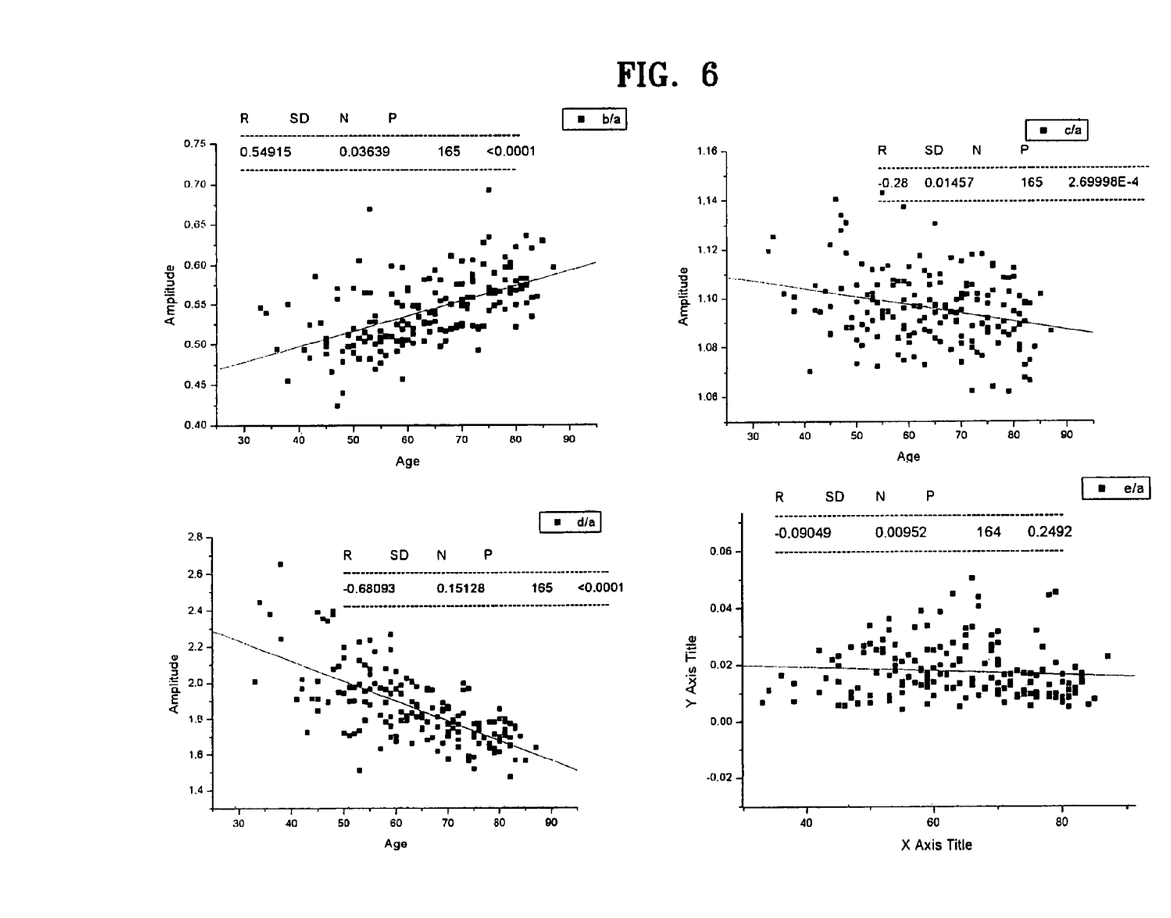
FIG. 6 are graphs of quantitative diagnostic indices for the degree of aging of blood vessels, which are applied in the present invention.

The method for calculating a degree of aging of blood vessels according to the present invention will now be described in detail with reference to FIG. 5. In the acceleration pulse waveform 502, "a" and "d" denote the start and end points, respectively, of a systolic contraction, and "e" denotes a diastolic contraction. Reference symbols "b" and "c" indicate additional inflection points. Value ratios at particular inflection points in the acceleration waveform, including d/a, b/a, c/a, e/a, (b- d- c- e)/a, etc., can be used as quantitative diagnostic indices for the degree of aging of blood vessels. FIG. 6 is four (4) graphs showing correlations of the diagnostic indices with age. As may be seen in FIG. 6, the index b/a is linearly proportional to age, whereas the index d/a tends to be inversely proportional to age.

Referring back to FIG. 4, the data storage portion 406 stores the calculated results output from the hemoglobin concentration and oxygen saturation calculation portion 402, the pulse rate calculation portion 403, the respiration rate calculation portion 404, and the DOA calculation portion 405 and outputs a calculated result according to a control signal of the control unit 102.

Figure 7:
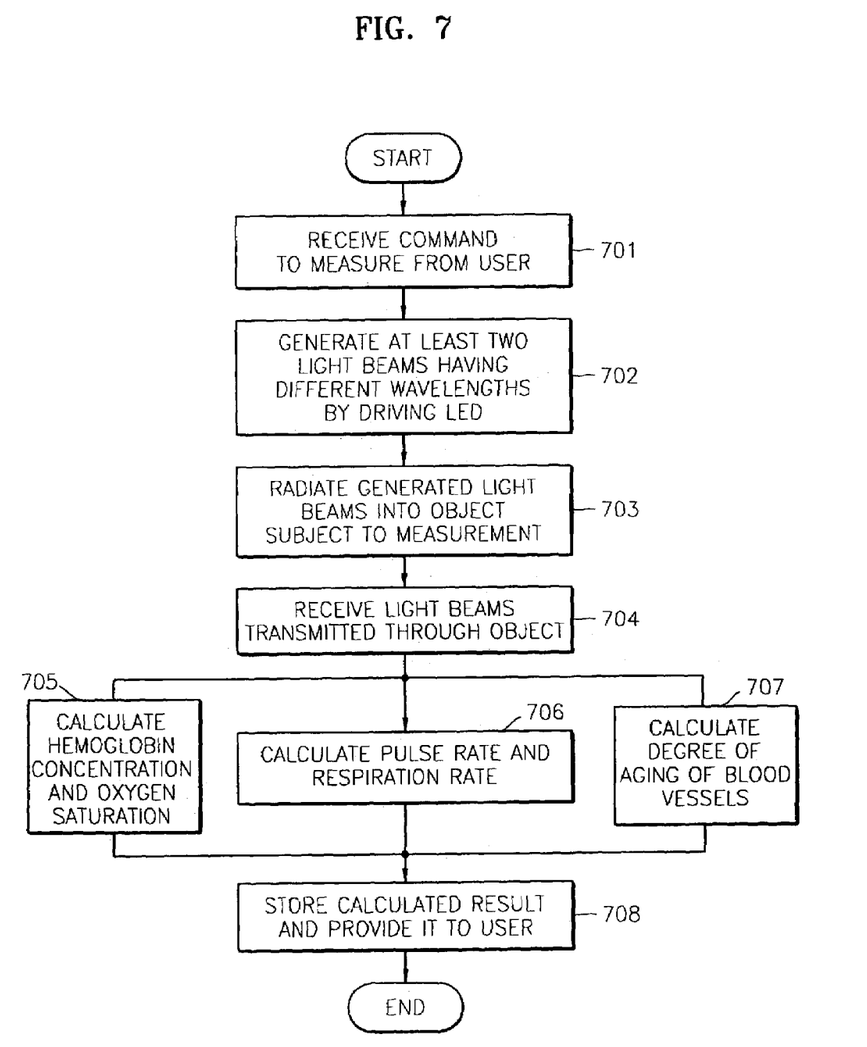
FIG. 7 is a flowchart illustrating a diagnosis method using light, according to an embodiment of the present invention.

FIG. 7 is a flowchart illustrating a diagnostic method using light, according to an embodiment of the present invention. Initially, in step 701, at least one parameter to be measured, which may include blood hemoglobin concentration, oxygen saturation, pulse rate, respiration rate, or degree of aging of blood vessels, is received from a user. Next, in step 702, an LED generating light required to measure a desired parameter is driven to generate at least two light beams having different wavelengths. The generated light beams are radiated onto a part of a subject's body, for example, a finger. In step 704, the light beams transmitted through the object are received for intensity measurement and the measured intensities of the light beams are converted into electrical signals. The electrical signals are used to calculate the parameter to be measured that is input by the user.

By using the methods described above, in step 705, hemoglobin concentration and oxygen saturation may be calculated, in step 706 pulse rate and respiration rate may be calculated, or, in step 707, degree of aging of blood vessels may be calculated. Next, in step 708, the calculated results may be stored and provided to the user.

Figure 8:
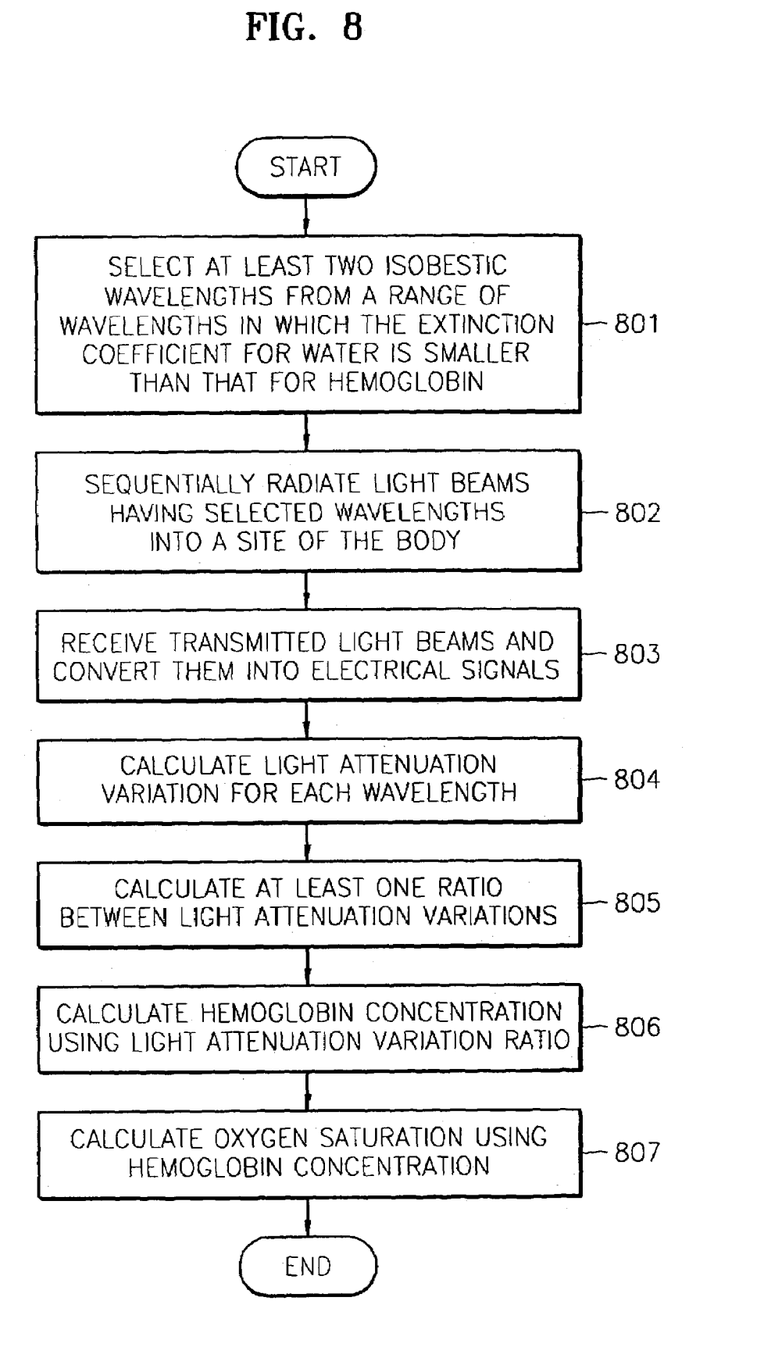
FIG. 8 is a flowchart illustrating a method for measuring hemoglobin concentration and oxygen saturation in step 705 of FIG. 7.

FIG. 8 is a flowchart illustrating a method for calculating hemoglobin concentration and oxygen saturation in step 705 of FIG. 7. Initially, in step 801, at least two isobestic wavelengths are selected from a range of wavelengths, in which the extinction coefficient for water is smaller than that for hemoglobin. Next, in step 802, light beams having the selected wavelengths are sequentially radiated onto a predetermined site of the subject's body. In step 803, the light beams transmitted through the predetermined site of the subject's body are received using a photodetector and converted into electrical signals. In step 804, the light attenuation variation for each wavelength is calculated using the electrical signals. In step 805, at least one ratio between the calculated light attenuation variations is calculated. In step 806, hemoglobin concentration is calculated using the calculated light attenuation variation ratio. Next, in step 807, oxygen saturation is calculated using the calculated hemoglobin concentration.

Figure 9:
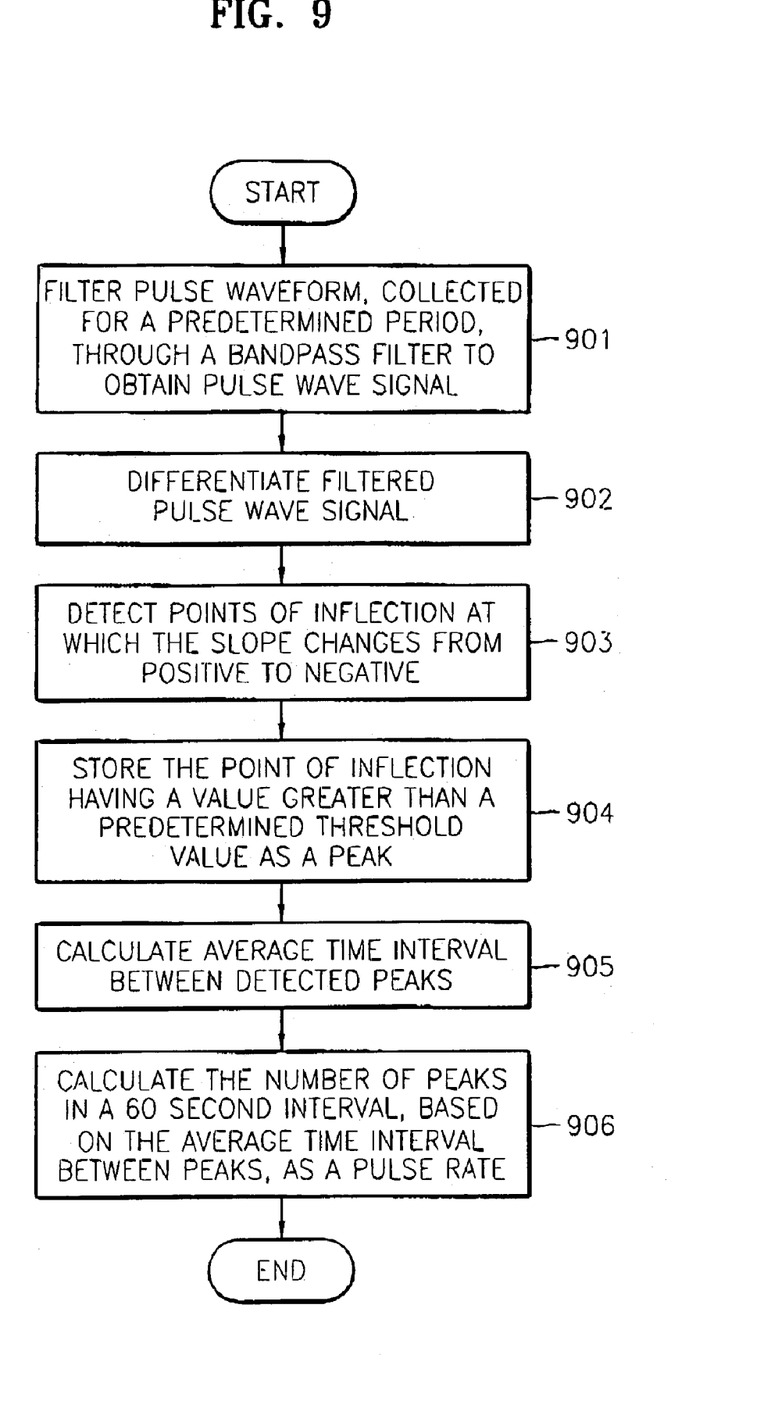
FIG. 9 is a flowchart illustrating a method for calculating pulse rate in step 706 of FIG. 7.

FIG. 9 is a flowchart illustrating a method for calculating pulse rate in step 706 of FIG. 7. In step 901, pulse wave data collected for a predetermined period is filtered through a bandpass filter to obtain a pulse wave signal. In step 902, the filtered pulse wave signal is differentiated. In step 903, inflection points, at which the slope changes from positive to negative, are detected from the differentiated pulse wave signal. The value of each of the inflection points is then compared with a predetermined threshold value. In step 904, if the value of an inflection point is greater than the predetermined threshold value, the inflection point is stored as a peak. In step 905, an average time interval between the detected peaks is calculated. In step 906, the number of peaks in a 60 second interval is calculated based on the average time interval between peaks, and the result is set as a pulse rate.

Figure 10:
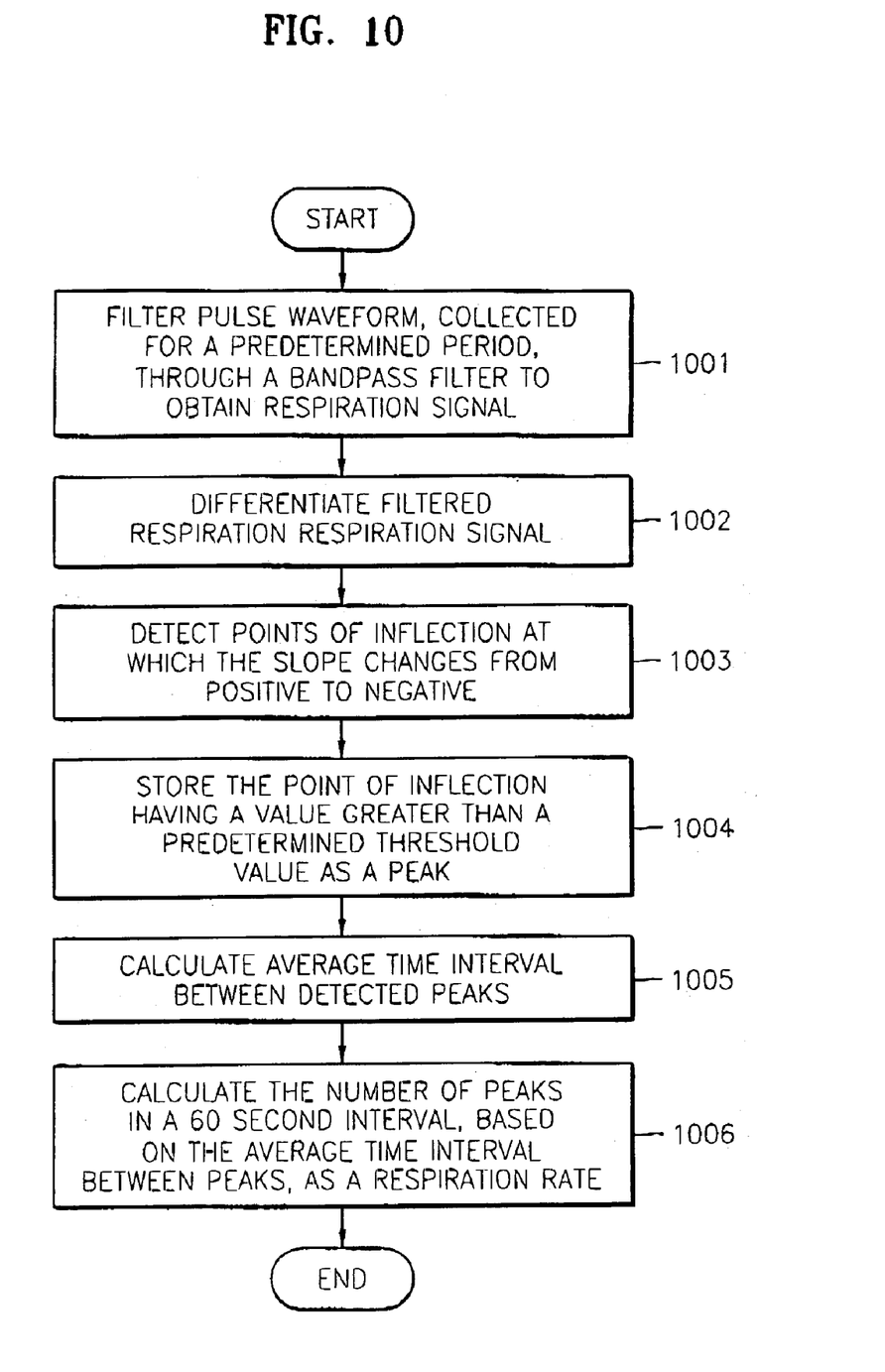
FIG. 10 is a flowchart illustrating a method for calculating respiration rate in step 706 of FIG. 7.

FIG. 10 is a flowchart illustrating a method for calculating respiration rate in step 706 of FIG. 7. In step 1001, pulse wave data collected for a predetermined period is filtered through a bandpass filter to obtain a respiration signal. In step 1002, the filtered respiration signal is differentiated. In step 1003, inflection points, at which the slope changes from positive to negative, are detected from the differentiated respiration signal. The value of each of the inflection points is then compared with a predetermined threshold value. In step 1004, if the value of an inflection point is greater than the predetermined threshold value, the inflection point is stored as a peak. In step 1005, an average time interval between the detected peaks is calculated. In step 1006, the number of peaks in a 60 second interval is calculated based on the average time interval between peaks, and the result is set as a respiration rate.

Figure 11:
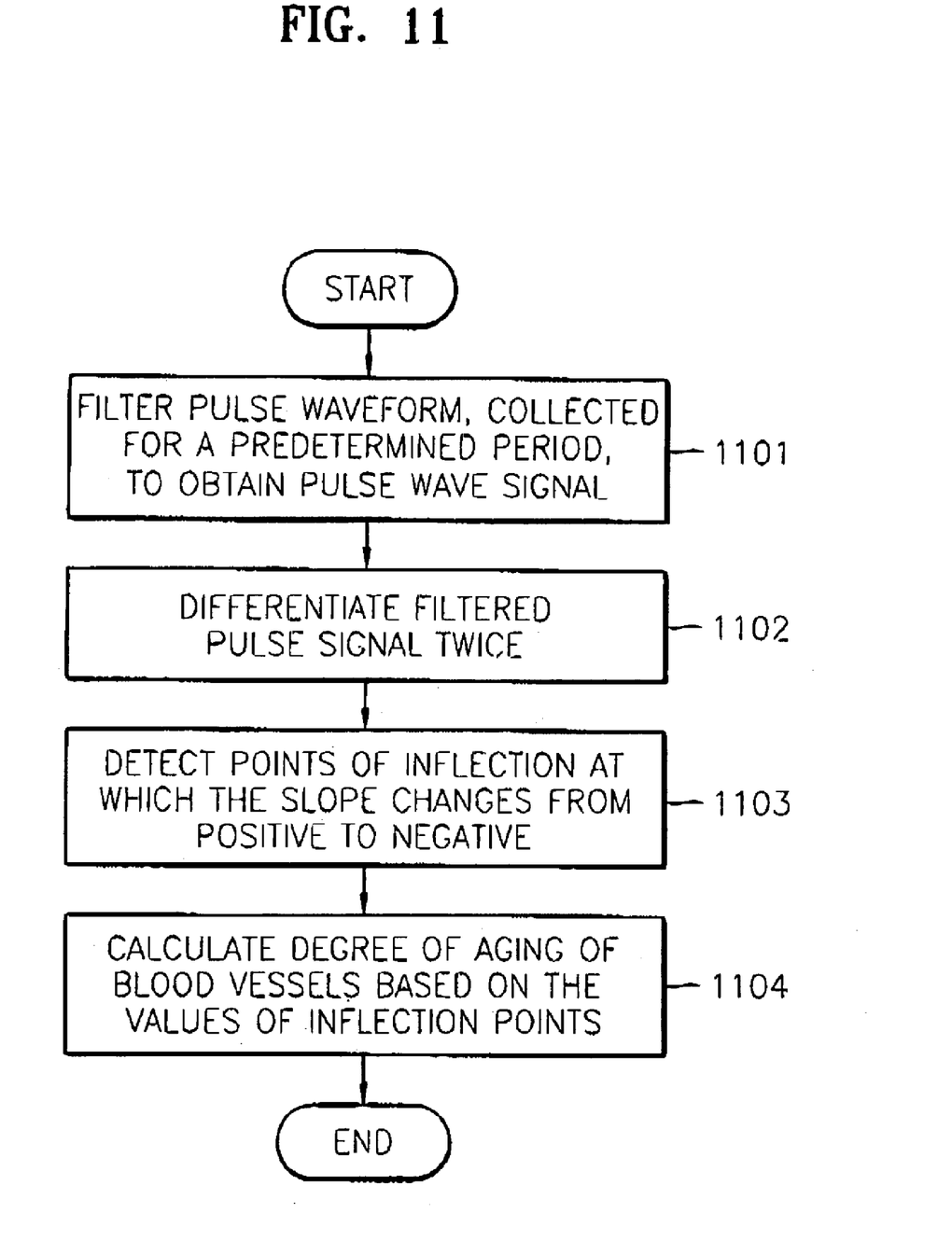
FIG. 11 is a flowchart illustrating a method for calculating degree of aging of blood vessels in step 707 of FIG. 7.

FIG. 11 is a flowchart illustrating a method for measuring degree of aging of blood vessels in step 707 of FIG. 7. Initially, in step 1101, pulse wave data collected for a predetermined period is filtered through a bandpass filter to obtain a pulse wave signal. In step 1102, the filtered pulse wave signal is differentiated twice into an acceleration pulse wave signal. In step 1103, inflection points, at which the slope changes from positive to negative, are detected from the accelerated pulse wave signal. Next, in step 1104, the degree of aging of blood vessels is calculated based on the values of the inflection points.

Light beams used in the present invention for measurement are selected from a range of wavelengths in which the extinction coefficient for water is smaller than that of hemoglobin, i.e., from wavelengths no longer than 1300 nm. At least two isobestic wavelengths, i.e., a wavelength having the same extinction coefficient for any forms of hemoglobin irrespective of whether hemoglobin is in oxidized or reduced form, are selected from that wavelength range. Accordingly, light beams having a wavelength of 422 nm, 453 nm, 499 nm, 529 nm, 546 nm, 569 nm, 584 nm, 805 nm, or 1300 nm may be used in the present invention.

The above embodiments of the present invention may be embodied in a general purpose digital computer by running a program from a computer readable medium, which includes but is not limited to storage media such as magnetic storage media (e.g., ROM's, floppy disks, hard disks, etc.), optically readable media (e.g., CD-ROMs, DVDs, etc.), and carrier waves (e.g., transmissions over the Internet).

The present invention effects measurements of hemoglobin concentration, oxygen saturation, pulse rate, respiration rate, and degree of aging of blood vessels using the same apparatus in a non-invasive manner. A diagnosis apparatus using light, according to the present invention, is convenient to carry and use and enables simultaneous real-time monitoring of hemoglobin concentration, oxygen saturation, pulse rate, and respiration rate.

A diagnosis apparatus using light, according to the present invention, is able to measure multiple parameters including hemoglobin concentration, oxygen saturation, pulse rate, respiration rate, and degree of aging of blood vessels, without withdrawing blood from a patient, and is very convenient to use as compared to conventional apparatuses that separately measure each of the parameters separately. In addition, the ability to measure at least the five parameters listed above using a single apparatus is cost effective.

According to the present invention, since only one photodetector is used, measurements can be achieved with a higher degree of accuracy. Measurements of such parameters of interest are less affected by body tissues excluding blood vessels. With the installation of a communication device in a diagnosis apparatus according to the present invention, the result of a measurement performed at home can be directly transmitted to a hospital via the Internet. Therefore, there is no inconvenience of going to a hospital for a checkup. A patient at home may be directly informed of his/her state of health by a doctor at a hospital or other remote location.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A diagnosis apparatus using light, comprising:
   an input/output unit for receiving a command for measurement from a user and for providing information on the result of a measurement to the user;
   a control unit for receiving the command for measurement from the input/output unit and for generating a control signal;
   a light generating unit for generating at least two light beams, each light beam having an initial intensity, for measurement according to the control signal;
   a light receiving unit for detecting the intensity of each of the at least two light beams after transmission through an object that is subject to measurement and for converting the received light beams into electrical signals; and
   a data processing unit for processing the electrical signals received from the light receiving unit and for outputting information on the result of a predetermined measurement to the input/output unit, the data processing unit including a degree of aging of blood vessels calculation portion for receiving the electrical signals from the light receiving unit, for extracting a first pulse wave signal having a frequency corresponding to an average pulse rate per minute for humans from the received electrical signals, for differentiating the extracted first pulse wave signal into a second pulse wave signal to detect inflection points therein, for calculating a diagnostic index for the degree of aging of blood vessels using the values of the inflection points, and for calculating a degree of aging of blood vessels using the calculated diagnostic index, based on a correlation between the degrees of aging of blood vessels and diagnostic indices therefor.

2. The diagnosis apparatus as claimed in claim 1, wherein the light generating unit comprises:
   a digital-to-analog converter for receiving the control signal from the control unit and for converting the received control signal into an analog signal;
   a light emitting diode driver for driving a light emitting diode to generate the at least two light beams according to the analog signal; and
   a light radiator for radiating the generated light beams onto the object.

3. The diagnosis apparatus as claimed in claim 1, wherein the light receiving unit comprises:
   a photodetector for detecting the intensities of the at least two light beams after transmission through the object and for converting the detected light beam intensities into analog electrical signals;
   a low-pass filter for filtering out a high frequency component of the analog electrical signals; and
   an analog-to-digital converter for converting the analog electrical signals into digital electrical signals.

4. The diagnosis apparatus as claimed in claim 1, wherein the data processing unit comprises:
   a data storage portion for storing measured results and for outputting to the input/output unit a calculated result according to a control signal of the control unit.

5. The diagnosis apparatus as claimed in claim 1, wherein the at least two light beams have different wavelengths.

6. The diagnosis apparatus as claimed in claim 1, wherein the at least two light beams are selected from a range of wavelengths in which the extinction coefficient for water is smaller than that of hemoglobin.

7. The diagnosis apparatus as claimed in claim 1, wherein each of the at least two light beams have a wavelength no longer than 1300 nm.

8. The diagnosis apparatus as claimed in claim 1, wherein the at least two light beams are isobestic.

9. The diagnosis apparatus as claimed in claim 1, wherein each of the at least two light beams has a wavelength selected from the group consisting of 422 nm, 453 nm, 499 nm, 529 nm, 546 nm, 569 nm, 584 nm, 805 nm, and 1300 nm.

10. The diagnosis apparatus as claimed in claim 1, wherein the data processing unit further comprises:
    a ratio calculation portion for receiving the electrical signals from the light receiving unit and for calculating, for each wavelength of the at least two light beams, a ratio of the intensity of the light received by the light receiving unit with respect to the initial intensity of the light radiated from the light generating unit; and
    a hemoglobin concentration and oxygen saturation calculation portion for calculating a hemoglobin concentration value using the ratio calculated by the ratio calculation portion based on a correlation between light intensity variations and hemoglobin concentrations and for calculating an oxygen saturation value using the calculated hemoglobin concentration value.

11. The diagnosis apparatus as claimed in claim 1, wherein the data processing unit further comprises:
    a pulse rate calculation portion for receiving the electrical signals from the light receiving unit, for extracting a pulse wave signal having a frequency corresponding to an average pulse rate per minute for humans from the received electrical signals, and for calculating a pulse rate based on an average time interval between peaks detected from the extracted pulse wave signal.

12. The diagnosis apparatus as claimed in claim 1, wherein the data processing unit further comprises:
    a respiration rate calculation portion for receiving the electrical signals from the light receiving unit, for extracting a respiration signal having a frequency corresponding to an average respiration rate per minute for humans from the received electrical signals, and for calculating a respiration rate based on an average time interval between peaks detected from the extracted respiration signal.

13. A diagnosis method using light, comprising:
    (a) receiving a command for measurement from a user;
    (b) generating a control signal according to the received command for measurement;
    (c) generating at least two light beams, each light beam having an initial intensity, for measurement according to the control signal;
    (d) radiating the at least two light beams onto an object that is subject to measurement, detecting the intensities of the at least two light beams after transmission through the object, and converting the detected intensities of the at least two light beams into electrical signals; and
    (e) processing the electrical signals to obtain information on the result of a predetermined measurement, including
       extracting a first pulse wave signal having a frequency corresponding to an average pulse rate per minute for humans from the electrical signals obtained in (d);
       differentiating the extracted first pulse wave signal into a second pulse wave signal to detect inflection points therein;
       calculating a diagnostic index for the degree of aging of blood vessels using the values of the inflection points; and
       calculating a degree of aging of blood vessels using the calculated diagnostic index, based on a correlation between the degrees of aging of blood vessels and diagnostic indices therefor.

14. The diagnosis method as claimed in claim 13, wherein generating the at least two light beams comprises:
    (c1) receiving the control signal and converting the received control signal into an analog signal;
    (c2) generating the at least two light beams according to the analog signal; and
    (c3) radiating the generated light beams onto the object.

15. A computer readable medium having embodied thereon a computer program for the diagnosis method according to claim 14.

16. The diagnosis method as claimed in claim 13, wherein radiating the light beams onto an object comprises:
    (d1) detecting the intensities of the at least two light beams after transmission through the object and converting the detected light beam intensities into analog electrical signals;
    (d2) filtering out a high frequency component of the analog electrical signals; and
    (d3) converting the analog electrical signals into digital electrical signals.

17. A computer readable medium having embodied thereon a computer program for the diagnosis method according to claim 16.

18. The diagnosis method as claimed in claim 13, further comprising providing the result of the predetermined measurement to the user.

19. The diagnosis method as claimed in claim 18, wherein the user is remotely located from the object subject to measurement.

20. A computer readable medium having embodied thereon a computer program for the diagnosis method according to claim 18.

21. The diagnosis method as claimed in claim 13, further comprising:
  storing the information on the result of the predetermined measurement.

22. The diagnosis apparatus as claimed claim 13, wherein the at least two light beams have different wavelengths.

23. The diagnosis apparatus as claimed in claim 13, wherein the at least two light beams are selected from a range of wavelengths in which the extinction coefficient for water is smaller than that of hemoglobin.

24. The diagnosis apparatus as claimed in claim 13, wherein each of the at least two light beams have a wavelength no longer than 1300 nm.

25. The diagnosis apparatus as claimed in claim 13, wherein the at least two light beams are isobestic.

26. The diagnosis apparatus as claimed in claim 13, wherein each of the at least two light beams has a wavelength selected from the group consisting of 422 nm, 453 nm, 499 nm, 529 nm, 546 nm, 569 nm, 584 nm, 805 nm, and 1300 nm.

27. A computer readable medium having embodied thereon a computer program for the diagnosis method according to claim 13.

28. The diagnosis method as claimed in claim 13, wherein processing the electrical signals further comprises:
  calculating, for each wavelength of the at least two light beams, a ratio of the intensity of the light beam detected in (d) with respect to the initial intensity of the light generated in (c); and
  calculating a hemoglobin concentration value using the ratio of the intensity of the light beam based on a correlation between light intensity variations and hemoglobin concentrations and calculating an oxygen saturation value using the calculated hemoglobin concentration value.

29. A computer readable medium having embodied thereon a computer program for the diagnosis method according to claim 28.

30. The diagnosis method as claimed in claim 13, wherein processing the electrical signals further comprises:
  extracting a pulse wave signal having a frequency corresponding to an average pulse rate per minute for humans from the electrical signals obtained in (d); and
  calculating a pulse rate based on an average time interval between peaks detected from the extracted pulse wave signal.

31. A computer readable medium having embodied thereon a computer program for the diagnosis method according to claim 30.

32. The diagnosis method as claimed in claim 13, wherein processing the electrical signals further comprises:
  extracting a respiration signal having a frequency corresponding to an average respiration rate per minute for humans from the electrical signals obtained in (d); and
  calculating a respiration rate based on an average time interval between peaks detected from the extracted respiration signal.

33. A computer readable medium having embodied thereon a computer program for the diagnosis method according to claim 32.

* * * * *